United States Patent
Kim et al.

(10) Patent No.: US 12,234,490 B2
(45) Date of Patent: Feb. 25, 2025

(54) COMPOSITION FOR PRIME EDITING COMPRISING PEGRNA FOR EDITING MUTATION OF ALPHA-1 ANTITRYPSIN DEFICIENCY

(71) Applicant: INDUSTRY-ACADEMIC COOPERATION FOUNDATION, YONSEI UNIVERSITY, Seoul (KR)

(72) Inventors: Hyongbum Henry Kim, Seoul (KR); Minyoung Lee, Seoul (KR); Yoo Jin Chang, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 10 days.

(21) Appl. No.: 18/170,035

(22) Filed: Feb. 16, 2023

(65) Prior Publication Data
US 2023/0332121 A1     Oct. 19, 2023

(30) Foreign Application Priority Data
Feb. 18, 2022  (KR) .......................... 10-2022-0021737

(51) Int. Cl.
| | |
|---|---|
| *C12N 9/22* | (2006.01) |
| *A61P 35/00* | (2006.01) |
| *C12N 15/10* | (2006.01) |
| *C12N 15/86* | (2006.01) |

(52) U.S. Cl.
CPC ................ *C12N 9/22* (2013.01); *A61P 35/00* (2018.01); *C12N 15/102* (2013.01); *C12N 15/86* (2013.01); *C12N 2310/20* (2017.05); *C12N 2740/15043* (2013.01)

(58) Field of Classification Search
CPC .. C12N 2310/20; C12N 15/113; C12N 15/11; C12N 9/22; C12N 9/1276; A61K 48/00
See application file for complete search history.

(56) References Cited

U.S. PATENT DOCUMENTS

2020/0216843 A1*  7/2020  Shen ...................... C12N 15/86

OTHER PUBLICATIONS

Liu et al., Apr. 9, 2021, "Improved prime editors enable pathogenic allele correction and cancer modelling in adult mice", Nature Communications, (2021) 12:2121, p. 1-13 and Supplementary Information (Year: 2021).*

(Continued)

*Primary Examiner* — Jennifer Dunston
*Assistant Examiner* — Jenna L Persons
(74) *Attorney, Agent, or Firm* — Oblon, McClelland, Maier & Neustadt, L.L.P.

(57) ABSTRACT

Provided is a genome editing composition for prime editing including a prime editor protein and a prime editing guide RNA, for editing a Z-type mutation of alpha-1 antitrypsin deficiency. The composition according to an aspect includes both a pegRNA sequence capable of effectively editing the SERPINA1 gene and prime editor 2 (PE 2), and thus, may effectively deliver the prime editor to a cell, and act specifically for a target sequence of the SERPINA1 gene, enabling genome editing with high accuracy, and therefore, may be useful as a SERPINA1 gene editing platform. In addition, the composition is capable of correcting the Z-type mutation of the SERPINA1 gene, and may be used for treatment or prevention of alpha-1 antitrypsin deficiency.

5 Claims, 4 Drawing Sheets

Specification includes a Sequence Listing.

(56) References Cited

OTHER PUBLICATIONS

Kim et al., Sep. 21, 2020, "Predicting the efficiency of prime editing guide RNAs in human cells" Nature Biotechnology, 39, p. 198-206 and Methods (Year: 2020).*

Seixas and Marques, 2021, "Known Mutations at the Cause of Alpha-1 Antitrypsin Deficiency an Updated Overview of SERPINA1 Variation Spectrum" The Application of Clinical Genetics, 2021:14, p. 173-194 (Year: 2021).*

NM_001127701.1(SERPINA1):c. 1096G>A (p.Glu366Lys), ClinVar, first entry Dec. 6, 2014, retrieved May 2, 2024 (Year: 2014).*

Anzalone et al., Dec. 5, 2019, "Search-and-replace genome editing without double-strand breaks or donor DNA" Nature, 576, p. 149-157, Methods, Extended Data and Supplementary Information (Year: 2019).*

Schene et al., Oct. 23, 2020, "Prime editing for functional repair in patient-derived disease models" Nature Communications, (2020)11:5352, p. 1-8 and Supplemental Information (Year: 2020).*

Habib et al., Jan. 8, 2022, "Comprehensive analysis of prime editing outcomes in human embryonic stem cells" Nucleic Acids Research, 50(2), p. 1187-1197 and Supplementary Information (Year: 2022).*

Lung, G. (2021). Precise correction of A1AT E342K by modified NGA PAM prime editing and determination of prime editing inhibition by TREX2 (Order No. 28771965). Available from ProQuest Dissertations & Theses Global. (2596320346). (Year: 2021).*

Truong et al., "Development of an intein-mediated split-Cas9 system for gene therapy", Nucleic Acids Research, 2015, vol. 43, No. 13, pp. 6450-6458.

Liu et al., "Improved prime editors enable pathogenic allele correction and cancer modelling in adult mice", Nature Communications (2021) 12:2121, pp. 1-13.

Schene et al., "Prime editing for functional repair in patient-derived disease models", Nature Communications (2020) 11:5352, pp. 1-8.

Wu et al., "Advances in CRISPR/Cas-based Gene Therapy in Human Genetic Diseases", Theranostics 2020, vol. 10, Issue 10, pp. 4374-4382.

Korean Office Action issued Feb. 13, 2024 in Korean Application 10-2022-0021737, (with English translation), 10 pages.

Habib, O. et al., "Comprehensive analysis of prime editing outcomes in human embryonic stem cells", Nucleic Acids Research, vol. 50, No. 2, 2022, 1187-1197.

* cited by examiner

SEQUENCE LISTING

```
Sequence total quantity: 7
SEQ ID NO: 1            moltype = DNA  length = 122
FEATURE                 Location/Qualifiers
source                  1..122
                        mol_type = other DNA
                        organism = Synthetic Construct
SEQUENCE: 1
ggcttcagtc cctttcttgt gttttagagc tagaaatagc aagttaaaat aaggctagtc   60
cgttatcaac ttgaaaaagt ggcaccgagt cggtgcgcta accattgacg agaaagggac  120
tg                                                                 122

SEQ ID NO: 2            moltype = DNA  length = 20
FEATURE                 Location/Qualifiers
source                  1..20
                        mol_type = other DNA
                        organism = Synthetic Construct
SEQUENCE: 2
ggcttcagtc cctttcttgt                                               20

SEQ ID NO: 3            moltype = DNA  length = 76
FEATURE                 Location/Qualifiers
source                  1..76
                        mol_type = other DNA
                        organism = Synthetic Construct
SEQUENCE: 3
gttttagagc tagaaatagc aagttaaaat aaggctagtc cgttatcaac ttgaaaaagt   60
ggcaccgagt cggtgc                                                   76

SEQ ID NO: 4            moltype = DNA  length = 26
FEATURE                 Location/Qualifiers
source                  1..26
                        mol_type = other DNA
                        organism = Synthetic Construct
SEQUENCE: 4
gctaaccatt gacgagaaag ggactg                                        26

SEQ ID NO: 5            moltype = DNA  length = 4158
FEATURE                 Location/Qualifiers
``` source                  1..4158
                        mol_type = other DNA
                        organism = Synthetic Construct
SEQUENCE: 5
atgaaacgga cagccgacgg aagcgagttc gagtcaccaa agaagaagcg gaaagtcgac   60
aagaagtaca gcatcggcct ggacatcggc accaactctg tgggctgggc cgtgatcacc  120
gacgagtaca aggtgcccag caagaaattc aaggtgctgg gcaacaccga ccggcacagc  180
atcaagaaga acctgatcgg agccctgctg ttcgacagcg gcgaaacagc cgaggccacc  240
cggctgaaga gaaccgccag aagaagatac accagacgga agaaccggat ctgctatctg  300
caagagatct tcagcaacga gatggccaag gtggacgaca gcttcttcca cagactggaa  360
gagtccttcc tggtggaaga ggataagaag cacgagcggc accccatctt cggcaacatc  420
gtggacgagg tggcctacca cgagaagtac cccaccatct accacctgag aaagaaactg  480
gtggacagca ccgacaaggc cgacctgcgg ctgatctatc tggccctggc ccacatgatc  540
aagttccggg gccacttcct gatcgagggc gacctgaaca cggacaacag cgacgtggac  600
aagctgttca tccagctggt gcagacctac aaccagctgt tcgaggaaaa ccccatcaac  660
gccagcggcg tggacgccaa ggccatcctg tctgccagac tgagcaagag cagacggctg  720
gaaaatctga tcgcccagct gcccggcgag aagaagaatg gcctgttcgg aaacctgatt  780
gccctgagcc tgggcctgac ccccaacttc aagagcaact tcgacctggc cgaggatgcc  840
aaactgcagc tgagcaagga cacctacgac gacgacctgg acaacctgct ggcccagatc  900
ggcgaccagt acgccgacct gtttctggcc gccaagaacc tgtccgacgc catcctgctg  960
agcgacatcc tgagagtgaa caccgagatc accaaggccc ccctgagcgc ctctatgatc 1020
aagagatacg acgagcacca ccaggacctg acccttgctga aagctctcgt gcggcagcag 1080
ctgcctgaga agtacaaaga gattttcttc gaccagagca agaacggcta cgccggctac 1140
attgacggcg gagccagcca ggaagagttc tacaagttca tcaagcccat cctggaaaag 1200
atggacggca ccgaggaact gctcgtgaag ctgaacagag aggacctgct gcggaagcag 1260
cggaccttcg acaacggcag catcccccac cagatccacc tgggagagct gcacgccatt 1320
ctgcggcggc aggaagattt ttacccattc ctgaaggaca accgggaaaa gatcgagaag 1380
atcctgacct tccgcatccc ctactacgtg ggccctctgg ccaggggaaa cagcagattc 1440
gcctggatga ccagaaagag cgaggaaacc atcaccccct ggaacttcga ggaagtggtg 1500
gacaagggcg cttccgccca gagcttcatc gagcggatga caaacttcga taagaacctg 1560
cccaacgaga aggtgctgcc caagcacagc ctgctgtacg agtacttcac cgtgtataac 1620
gagctgacca aagtgaaata cgtgaccgag ggaatgagaa agcccgcctt cctgagcggc 1680
gagcagaaaa aggccatcgt ggacctgctg ttcaagacca ccggaaagt gaccgtgaag 1740
cagtcgaaag aggactactt caagaaaatc gagtgcttcg actccgtgaa aatctccggc 1800
gtggaagatc ggttcaacgc ctcccctggc acataccacg atctgctgaa aattatcaag 1860
gacaaggact tcctggacaa tgaggaaaac gaggacattc tggaagatat cgtgctgacc 1920
ctgacactgt ttgaggacag agagatgatc gaggaacggc tgaaaaccta tgcccacctg 1980
ttcgacgaca agtgatgaa gcagctgaag cggcggagat acaccggctg gggcaggctg 2040
agccggaagc tgatcaacgg catccgggac aagcagtccg gcaagacaat cctggatttc 2100
ctgaagtccg acggcttcgc caacagaaac ttcatgcagc tgatccacga cgacagcctg 2160
acctttaaag aggacatcca gaaagcccag gtgtccggcc agggcgatag cctgcacgag 2220
cacattgcca atctggccgg cagccccgcc attaagaagg catcctgca gacagtgaag 2280
gtggtggaa gctcgtgaa agtgatgggc cggcacaagc ccgagaacat cgtgatcgaa 2340
atggccagag agaaccagac cacccagaag ggacagaaga cagccgcga gagaatgaag 2400
cggatcgaag agggcatcaa agagctgggc agccagatcc tgaaagaaca ccccgtggaa 2460
aacacccagc tgcagaacga gaagctgtac ctgtactacc tgcagaatgg gcgggatatg 2520
tacgtggacc aggaactgga catcaaccgg ctgtccgact acgatgtgga cgctatcgtg 2580
cctcagagct ttctgaagga cgactccatc gacaacaagg tgctgaccag aagcgacaag 2640
aaccggggca gagcgacaa cgtgccctcc aagaggtcg tgaagaagat gaagaactac 2700
tggcggcagc tgctgaacgc caagctgatt acccagagaa agttcgacaa tctgaccaag 2760
gccgagagag cggcctgag cgaactggat aaggccgct tcatcaagag acagctggtg 2820
gaaacccggc agatcacaaa gcacgtggca cagatcctgg actcccggat gaacactaag 2880
tacgacgaga atgacaagct gatccgggaa gtgaaagtga tcaccctgaa gtccaagctg 2940
gtgtccgatt tccggaagga tttccagttt tacaaagtgc gcgagatcaa caactaccac 3000
cacgcccacg acgcctacct gaacgccgtc gtgggaaccg ccctgatcaa aaagtaccct 3060
aagctggaaa gcgagttcgt gtacggcgac tacaaggtgt acgacgtgcg gaagatgatc 3120
gccaagagcg agcaggaaat cggcaaggct accgccaagt acttcttcta cagcaacatc 3180
atgaactttt tcaagaccga gattaccctg gccaacggcg agatccggaa gcggcctctg 3240
atcgagacaa acggcgaaac cggggacgtc gtgtgggata agggccggga ttttgccacc 3300
gtgcgaaag tgctgagcat gccccaagtg aatatcgtga aaagacgga ggtgcagaca 3360
ggcggcttca gcaaagagtc tatcctgccc aagaggaaca gcgataagct gatcgccaga 3420
aagaaggact gggaccctaa gaagtacggc ggcttcgaca cccccaccgt ggcctattct 3480
gtgctggtgg tggccaaagt ggaaaaggc aagtccaaga aactgaagag tgtgaaagag 3540
ctgctgggga tcaccatcat ggaaagaagc agcttctga agatcccat cgacttctg 3600
gaagccaagg gctacaaaga agtgaaaaag gacctgatca tcaagctgcc taagtactcc 3660
ctgttcgagc tggaaaacgg ccggaagaga atgctggcct ctgccggcga actgcagaag 3720
ggaaacgaac tggccctgcc ctccaaatat gtgaacttcc tgtacctggc cagccactat 3780
gagaagctga agggctcccc cgaggataat gagcagaaac agctgtttgt ggaacagcac 3840
aagcactacc tggacgagat catcgagcag atcagcgagt tctccaagag agtgatcctg 3900
gccgacgcta atctggacaa agtgctgtcc gcctacaaca agcaccggga taagcccatc 3960
agagcagg ccgagaatat catccacctg tttacctga caatctggg agcccctgcc 4020
gccttcaagt actttgacac caccatcgac cggaagaggt acaccagcac caaagaggtg 4080
ctggacgcca ccctgatcca ccagagcatc accggctgt acgagacacg gatcgacctg 4140
tctcagctgg gaggtgac                                                4158

SEQ ID NO: 6            moltype = DNA   length = 4158
FEATURE                 Location/Qualifiers
source                  1..4158
                        mol_type = other DNA organism = Synthetic Construct
SEQUENCE: 6

```
atgaaacgga cagccgacgg aagcgagttc gagtcaccaa agaagaagcg gaaagtcgac   60
aagaagtaca gcatcggcct ggacatcggc accaactctg tgggctgggc cgtgatcacc  120
gacgagtaca aggtgcccag caagaaattc aaggtgctgg gcaacaccga ccggcacagc  180
atcaagaaga acctgatcgg agccctgctg ttcgacagcg cgaaacagc cgaggccacc   240
cggctgaaga gaaccgccag aagaagatac accagacgga gaaccggat ctgctatctg   300
caagagatct tcagcaacga gatggccaag gtggacgaca gcttcttcca cagactggaa  360
gagtccttcc tggtggaaga ggataagaag cacgagcggc accccatctt cggcaacatc  420
gtggacgagg tggcctacca cgagaagtac cccaccatct accacctgag aaagaaactg  480
gtggacagca ccgacaaggc cgacctgcgg ctgatctatc tggccctggc ccacatgatc  540
aagttccggg gccacttcct gatcgaggc gacctgaacc cgacaacag cgacgtggac    600
aagctgttca tccagctggt gcagacctac aaccagctgt tcgaggaaaa ccccatcaac  660
gccagcggc gtggacgcca aggccatcct gctgccagac tgagcaagag cagacggctg   720
gaaaatctga tcgcccagct gccggcgag aagaagaatg gcctgttcgg aaacctgatt   780
gccctgagcc tgggcctgac ccccaacttc aagagcaact tcgacctgcc cgaggatgcc  840
aaactgcagc tgagcaagga cacctacgac gacgacctgg acaacctgct ggcccagatc  900
ggcgaccagt acgccgacct gtttctggcc gccaagaacc tgtccgacgc catcctgctg  960
agcgacatcc tgagagtgaa caccgagatc accaaggccc cctgagcgc ctctatgatc  1020
aagagatacg acgagcacca ccaggacctg accctgctga agctctcgt gcggcagcag  1080
ctgcctgaga agtacaaaga gattttcttc gaccagagca agaacggcta cgccggctac  1140
attgacggcg gagccagcca ggaagagttc tacaagttca tcaagcccat cctggaaaag  1200
atggacggca ccgaggaact gctcgtgaag ctgaacagag aggacctgct gcggaagcag  1260
cggaccttcg acaacggcag catcccccac cagatccacc tgggagagct gcacgccatt  1320
ctgcggcggc aggaagattt ttacccattc ctgaaggaca accggaaaaa gatcgagaag  1380
atcctgacct tccgcatccc ctactacgtg gccctctgg ccaggggaaa cagcagattc   1440
gcctggatga ccagaaagag cgaggaaacc atcaccccct ggaacttcga ggaagtggtg  1500
gacaaggcg cttccgccca gagcttcatc gagcggatga ccaacttcga taagaacctg   1560
cccaacgaca aggtgctgcc caagcacagc ctgctgtacg agtactttac cgtgtataac  1620
gagctgacca aagtgaaata cgtgaccgag ggaatgaaa agcccgcctt cctgagcggc   1680
gagcagaaaa aggccatcgt ggacctgctg ttcaagacca accggaaagt gaccgtgaag  1740
cagctgaaag aggactactt caagaaaatc gagtgcttcg actccgtgga aatctccggc  1800
gtggaagatc ggttcaacgc ctccctgggc ataccacg atctgctgaa aattatcaag    1860
gacaaggact tcctgacaa tgaggaaaac gaggacattc tggaagatat cgtgctgacc   1920
ctgacactgt tgaggacag agagatgatc gaggaacggc tgaaaccta tgcccacctg    1980
ttcgacgaca aagtgataaa gcagtgaag cggcggagat acaccggctg gggcaggctg   2040
agccggaagc tgatcaacgg catccgggac aagcagtccg gcaagacaat cctggatttc  2100
ctgaagtccg acggcttcgc caacagaaac ttcatgcagc tgatccacga cgacagcctg  2160
acctttaaag aggacatcca gaaagcccag gtgtccggcc agggcgatag cctgcacgag  2220
cacattgcca atctgccgg cagccccgcc attaagaagg catcctgca gacagtgaag    2280
gtggtggacg agctcgtgaa agtgatgggc cgcacaagc cgagaacat cgtgatcgaa    2340
atggccagag agaaccagac cacccagaag ggacagaaga cagccgcga gagaatgaag   2400
cggatccgaa agggcatcaa agagctgggc agccagatcc tgaaagaaca ccccgtggaa  2460
aacacccagc tgcagaacga gaagctgtac ctgtactacc tgcagaatgg gcgggatatg  2520
tacgtggacc aggaactgga catcaaccgg ctgtccgact acgatgtgga cgctatcgtg  2580
cctcagagct ttctgaagga cgactccatc gacaacaagg tgctgaccag aagcgacaag  2640
aaccggggca gagcgacaa cgtgccctcc aagaggtcg tgaagaagat gaagaactac    2700
tggcggcagc tgctgaacgc caagctgatt acccagagaa agttcgacaa tctgaccaag  2760
gccgagagag gcggcctgag cgaactggat aaggccggct tcatcaagag acagctggtg  2820
gaaaccggc agatcacaaa gcacgtggca cagatcctgg actcccggat gaacactaag  2880
tacgacgagc atgacaagct gatccggaa gtgaaagtga tcaccctgaa gtccaagctg   2940
gtgtccgatt tccggaagga tttccagttt tacaaagtgc gcgagatcaa caactaccac  3000
cacgcccacg acgcctacct gaacgccgtc gtgggaaccg ccctgatcaa aaagtaccct  3060
aagctgaaaa gcgagttcgt gtacggcgac tacaaggtgt acgacgtgcg gaagatgatc  3120
gccaagagcg agcaggaaat cggcaaggct accgccaagt acttcttcta cagcaacatc  3180
atgaactttt tcaagaccga gattaccctg gccaacggcg agatccggaa gcggcctctg  3240
atcgagacaa acggcgaaac cggggagatc gtgtgggata agggccggga ttttgccacc  3300
gtgcggaaag tgctgagcat gccccaagtg aatatcgtga aaaagaccga ggtgcagaca  3360
ggcggcttca gcaaagagtc tatcaggccc aagaggaaca gcgataagct gatcgccaga  3420
aagaaggact gggaccctaa gaagtacggc ggcttcgtca gccccaccgt ggcctattct  3480
gtgctggtgg tggccaaagt ggaaaagggc aagtccaaga aactgaagag tgtgaaagag  3540
ctgctgggga tcaccatcat ggaaagaagc agcttcgaga agaatccat cgactttctg   3600
gaagccaagg gctacaaaga agtgaaaaag gacctgatca tcaagctgcc taagtactcc  3660
ctgttcgagc tggaaaacgg ccggaagaga atgctggcct gccagatt cctgcagaag    3720
ggaaacgaac tggccctgcc ctccaaatat gtgaacttcc tgtacctggc cagccactat  3780
gagaagctga agggctcccc cgaggataat gagcagaaac agctgtttgt ggaacagcac  3840
aagcactacc tggacgagat catcgagcag atcagcgagt ctccaagag agtgatcctg   3900
gccgacgcta tcggacaa agtgctgtcc gcctacaaca gcaccggga taagcccatc    3960
agagcagg ccgagaatat catccacctg tttacccctga ccaatctggg agcccctagg  4020
gccttcaagt actttgacac caccatcgac cggaaggtgt acaggagcac caaagaggtg  4080
```

```
ctggacgcca ccctgatcca ccagagcatc accggcctgt acgagacacg gatcgacctg    4140
tctcagctgg gaggcgac                                                  4158

SEQ ID NO: 7            moltype = DNA  length = 20
FEATURE                 Location/Qualifiers
source                  1..20
                        mol_type = other DNA
                        organism = Synthetic Construct
SEQUENCE: 7
agcttcagtc cctttcttgt                                                  20
```

COMPOSITION FOR PRIME EDITING COMPRISING PEGRNA FOR EDITING MUTATION OF ALPHA-1 ANTITRYPSIN DEFICIENCY

REFERENCE TO A SEQUENCE LISTING

In accordance with WIPO Standard ST.26 and pursuant to 37 C.F.R. 1.831-1.835, the specification makes reference to a Sequence Listing submitted electronically as a .xml file named "546778US_ST26new". The .xml file was generated on Jul. 3, 2023, and is 15,750 bytes in size. The entire contents of the Sequence Listing are hereby incorporated by reference.

CROSS-REFERENCE TO RELATED APPLICATION

This application claims the benefit of Korean Patent Application No. 10-2022-0021737, filed on Feb. 18, 2022 in the Korean Intellectual Property Office, the disclosure of which is incorporated herein in its entirety by reference.

BACKGROUND

1. Field

The present disclosure relates to a genome editing composition for prime editing including a prime editor protein and prime editing guide RNA for editing a Z-type mutation of alpha-1 antitrypsin deficiency.

2. Description of the Related Art

Alpha-1 antitrypsin deficiency is a genetic disease caused by mutations in a SERPINA1 gene, mainly affecting the liver and lungs. Among various mutation types, in a case of a Z-type mutation of the SERPINA1 gene, alpha-1 antitrypsin proteins with an abnormal structure synthesized in hepatocytes are not excreted and accumulates inside the cells, resulting in liver diseases such as hepatitis and cirrhosis. In addition, due to deficiency of alpha-1 antitrypsin in the blood, a probability of developing lung diseases such as chronic obstructive pulmonary disease increases. In terms of frequency of occurrence, it is known that about 1 in 2,500 of the European population suffers from this disease, and the disease is relatively rare in Asia. Since it is a genetic disease, there is currently no fundamental clinical treatment, and only symptomatic treatment is possible.

A prime editor is a type of genetic scissors system based on CRISPR/Cas9 derived from a bacterial immune system. Usually, wild-type Cas9 causes DNA double strand breaks in a genome in a specific sequence complementary to a guide RNA. The prime editor is capable of editing a specific sequence in a genome as desired without damaging the double strand, by using a Cas9 nickase, a reverse transcriptase, and a prime editing guide RNA (pegRNA), instead of wildtype Cas9. As with other genetic scissors, gene editing efficiency of the prime editor is greatly affected by the pegRNA, and it is important to select an optimal pegRNA for specific gene editing. In addition, it is also important to form an optimal complex by using this pegRNA with an optimal prime editor (PE) protein.

Researches on such issues have been actively conducted for well-established genetic scissors such as the CRISPR/Cas system, but methods of treating genetic diseases such as alpha-1 antitrypsin deficiency by using the prime editor have been barely researched.

SUMMARY

An aspect is to provide a composition for editing a Z-type mutation of a SERPINA1 gene, including: a recombinant vector expressing a prime editor protein or a variant of the prime editor protein, the prime editor protein including a nucleic acid sequence encoding a Cas9 nickase-reverse transcriptase; and a recombinant vector including a prime editing guide RNA (pegRNA) sequence.

Another aspect is to provide a kit for editing the Z-type mutation of the SERPINA1 gene, including the above composition.

Another aspect is to provide a pharmaceutical composition for treatment or prevention of alpha-1 antitrypsin deficiency, including the above composition.

Still another aspect is to provide a method of editing the Z-type mutation of the SERPINA1 gene, the method including introducing respective recombinant vectors into isolated eukaryotic cells or eukaryotic organisms except for human, wherein the recombinant vectors include: a recombinant vector expressing a prime editor protein or a variant of the prime editor protein, the prime editor protein including a nucleic acid sequence encoding a Cas9 nickase-reverse transcriptase; and a recombinant vector including a prime editing guide RNA (pegRNA) sequence.

Additional aspects will be set forth in part in the description which follows and, in part, will be apparent from the description, or may be learned by practice of the presented embodiments.

An aspect provides a composition for editing a Z-type mutation of the SERPINA1 gene, including: a recombinant vector expressing a prime editor protein or a variant of the prime editor protein, the prime editor protein including a nucleic acid sequence encoding a Cas9 nickase-reverse transcriptase; and a recombinant vector including a prime editing guide RNA (pegRNA) sequence.

The term "editing" refers to deleting, changing, and/or restoring (altering) a gene function by deletion, insertion, substitution, etc. of at least one nucleic acid molecule (for example, about 1 bp to about 100,000 bp, about 1 bp to about 10,000 bp, about 1 bp to about 1,000 bp, about 1 bp to about 100 bp, about 1 bp to about 70 bp, about 1 bp to about 50 bp, about 1 bp to about 30 bp, about 1 bp to about 20 bp, or about 1 bp to about 10 bp) by a cleavage at a target site of SERPINA1, a target gene, unless otherwise specified. In this specification, the genome editing may refer to prime editing.

The term "prime editing" refers to a genome editing method using the 4th generation genetic scissors, capable of introducing genetic changes by cleaving one strand of DNA without a DNA double-strand break.

Prime editing is performed by a "prime editor (PE)". The prime editor may be selected from the group consisting of PE1, PE2, PE3, and PE3b. In an embodiment, the prime editor may be PE2.

The variant of the prime editor protein is a variant retaining functions of the prime editor, and may specifically be a prime editor variant mutated to recognize NG-PAM or a prime editor variant mutated to recognize NGG-PAM.

The prime editor variant mutated to recognize NGG-PAM may be, for example, wild-type PE2, specifically, NGG-PAM-Cas9 nickase H840A including a polynucleotide consisting of SEQ ID NO: 5. The prime editor variant mutated to recognize NG-PAM may be one in which a specific nucleic acid sequence is modified at the C-terminus portion of a Cas9 nickase domain of the wild-type PE2. For example, the prime editor variant mutated to recognize NG-PAM may include at least one substitution selected from: substitution of CT, which are the 3385th to 3386th nucleotides in a nucleotide sequence of a wildtype NGG-PAM-Cas9-nickase, to AG; substitution of A, which is the 3458th nucleotide in a nucleotide sequence of a wildtype NGG-PAM-Cas9-nickase, to T; substitution of G, which is the 3706th nucleotide in a nucleotide sequence of a wildtype NGG-PAM-Cas9-nickase, to A; substitution of CGAA, which are the 3708th to 3711th nucleotides in a nucleotide sequence of a wildtype NGG-PAM-Cas9-nickase, to ATTC; substitution of GCC, which are the 4018th to 4020th nucleotides in a nucleotide sequence of a wildtype NGG-PAM-Cas9-nickase, to AGG; substitution of AG, which are the 4057th to 4058th nucleotides in a nucleotide sequence of a wildtype NGG-PAM-Cas9-nickase, to GT; substitution of CC, which are the 4064th to 4065th nucleotides in a nucleotide sequence of a wildtype NGG-PAM-Cas9-nickase, to GG; and substitution of T, which is the 4155th nucleotide in a nucleotide sequence of a wildtype NGG-PAM-Cas9-nickase, to C. Specifically, the prime editor variant mutated to recognize NG-PAM may be, for example, NG-PAM-Cas9 nickase H840A including a polynucleotide consisting of SEQ ID NO: 6.

The term "Cas9 nickase" used in a prime editor may be modified to nick a single strand of DNA.

The prime editor may include a prime editor (PE) protein and a prime editing guide RNA (pegRNA), wherein, in the prime editor protein, a nickase Cas9 (nCas9) and a reverse-transcriptase (RT) are fused. In the present specification, the "prime editor" in a narrow sense may mean a prime editor protein in which nCas9 and an RT are fused, and the term in a broader sense may mean a prime editor complex in which the prime editor protein, a pegRNA, and/or a single guide RNA (sgRNA) form a complex.

The "Cas9 protein" may have been modified to nick a strand of DNA. For example, the Cas9 protein may be nCas9, which is a mutant that can only nick single strands, but any modified Cas9 protein may be used, within a range that the Cas9 protein is modified to be delivered to a target sequence with a pegRNA and to target-specifically nick a single strand.

Prime editing occurs when the prime editor protein and the pegRNA form a complex. The sgRNA may be further introduced to maximize prime-editing efficiency, and the sgRNA is able to form a nick with a prime editor protein at a site a little away from a target gene region to which the pegRNA binds.

The term "reverse-transcriptase (RT)" refers to an enzyme that synthesizes new complementary DNA from an RNA template.

The term "prime editor", used herein, may merely mean to include a Cas9 nickase-RT fusion protein, or the term may mean to include both the Cas9 nickase-RT fusion protein and a pegRNA. For example, when a pegRNA is separately introduced into a cell, introducing a prime editor may mean introducing a Cas9 nickase-RT fusion protein only. That is, when a pegRNA is already introduced into a cell, introducing a prime editor may mean introducing a Cas9 nickase-RT fusion only.

The term "prime-editing guide RNA (pegRNA)" includes: a spacer sequence that recognizes a target sequence; a scaffold sequence; a primer-binding site (PBS) needed to initiate reverse transcription; and a reverse transcription (RT) template that includes a desired genetic modification. In the present specification, the term "spacer sequence" may be used interchangeably with the term "guide sequence".

The pegRNA sequence may be a polynucleotide including: a spacer region of SEQ ID NO: 2, a scaffold sequence region of SEQ ID NO: 3; and an RT template and a PBS of SEQ ID NO: 4.

In an embodiment, the pegRNA may consist of a nucleotide sequence of SEQ ID NO: 1.

TABLE 1

| pegRNA sequence (5' to 3') | SEQ ID NO: |
|---|---|
| GGCTTCAGTCCCTTTCTTGTGTTTTAGAGCTAGAAATAGCAAG TTAAAATAAGGCTAGTCCGTTATCAACTTGAAAAAGTGGCACC GAGTCGGTGCGCTAACCATTGACGAGAAAGGGACTG | 1 |

The underlined part represents the spacer sequence, the bolded sequence represents the scaffold sequence, and the italicized sequence represents the RT template and PBS sequence.

The SERPINA1 gene is known to be present in human chromosome 14, and the GenBank Accession number thereof is NC_000014.9. Those skilled in the art may easily identify a location and a sequence of the mutation by using this accession number. The specific sequence corresponding to the number registered in the UCSC genome browser or GenBank may change somewhat over time. It will be apparent to those skilled in the art that the scope of the present disclosure also extends to the altered sequence.

The term "target sequence" means a target nucleotide sequence targeted by a pegRNA. The target sequence may be a sequence expected to be targeted by the pegRNA, and may be, for example, a partial sequence of a genomic sequence known in the art, or a sequence arbitrarily designed by a person skilled in the art to analyze. Specifically, the target sequence targeted by a pegRNA of an aspect may be a sequence for correcting a Z-type mutation (c.1096 G to A) located in exon 7 of the human SERPINA1 gene, and may be a sequence corresponding to a length of about 20 bp, and more specifically, the target sequence may be a reverse complement sequence for c.1094-1113 of the SERPINA1 gene with the Z-type mutation, for example, the following sequence.

```
                                    (SEQ ID NO: 7)
      5'-AGCTTCAGTCCCTTTCTTGT-3'
```

The term "oligonucleotide" means a substance in which several to hundreds of nucleotides are linked by phosphodiester bonds. A length of the oligonucleotide may be about 100 nts to about 300 nts, about 100 nts to about 250 nts, or about 100 nts to about 200 nts, but is not limited thereto, and may be appropriately adjusted by those skilled in the art.

The nucleotide sequence encoding a pegRNA included in the oligonucleotide may include a spacer sequence, an RT template sequence, a PBS sequence, and the like.

The target nucleotide sequence included in the oligonucleotide may include a protospacer adjacent motif (PAM) and an RT template binding region. The RT template binding region may include a sequence completely or partially complementary to an RT template.

The oligonucleotide may further include a barcode sequence. Accordingly, the oligonucleotide may include a sequence encoding a pegRNA, a barcode sequence, and a target sequence targeted by the pegRNA. A number of the barcode sequence may be one, two, or more. The barcode sequence may be appropriately designed by those skilled in the art according to a purpose. For example, the barcode sequence may be such that each pair of a pegRNA and its corresponding target sequence may be identified after performing deep sequencing.

The oligonucleotide may further include an additional sequence to which primers may be bound for PCR amplification.

The term "library" means a group (pool or population) including two or more substances of the same kind with different properties. Thus, an oligonucleotide library may be a group including two or more types of oligonucleotides differing in nucleotide sequences, for example, two or more types of oligonucleotides differing in pegRNAs and/or target sequences. In addition, a cell library may be a group of two or more types of cells having different properties, for example, cells having different oligonucleotides included in the cells.

The term "vector" may refer to an expression vector capable of expressing a target protein in an appropriate host cell, and refers to a genetic construct including essential regulatory elements operably linked to express a gene insert. The "vector" may refer to a medium capable of delivering the oligonucleotide into a cell. Specifically, the vector may include an oligonucleotide including each sequence encoding a pegRNA, and a target sequence.

The term "operably linked" means that a regulatory sequence for nucleic acid expression and a nucleotide sequence encoding a protein of interest are functionally linked to perform general functions.

The vector may mean a medium capable of delivering a prime editor protein and a pegRNA into a cell. The vector may be a viral vector, or a plasmid vector, but is not limited thereto. The viral vector may be any one selected from, for example, lentiviral vectors, retroviral vectors, adenoviral vectors, adeno-associated viral vectors, and herpes simplex viral vectors, but is not limited thereto. Specifically, the viral vector may be a lentiviral vector.

The vector may include essential regulatory elements operably linked to an insert so that the insert, that is, an encoded nucleic acid sequence may be expressed, when the vector exists inside a cell of an organism. The vector may be manufactured and purified by using standard recombinant DNA techniques. A type of the vector is not particularly limited as long as the vector may function in desired cells such as prokaryotic cells and eukaryotic cells. The vector may include a promoter, an initiation codon, and a termination codon. In addition, DNA encoding a signal peptide, and/or an enhancer sequence, and/or a 5' or 3' untranslated region, and/or a selectable marker region, and/or a replication unit may also be appropriately included.

The term "promotor" refers to a DNA base sequence site to which transcriptional regulatory elements bind, and a promoter capable of inducing a powerful and stable gene expression may be used to increase a gene expression rate according to a purpose of the present disclosure.

A method of delivering the vector to a cell may be by using various methods known in the art. For example, various methods known in the art, such as local injection, microinjection, electroporation, lipofection, and the like may be used. Furthermore, when a viral vector is used, infection of virus particles may be used as a means to deliver an object, that is, the vector into cells. In addition, the vector may be introduced into the cells by gene gun bombardment, and the like. The introduced vector may exist in the cell as a vector itself or may be integrated into the chromosome, but its manner of existence is not limited thereto.

A type of cells into which the vector may be introduced may be appropriately selected by a person skilled in the art depending on a type of the vector and/or a type of desired cells, but examples may include bacterial cells such as *Escherichia coli*, *Streptomyces*, and *Salmonella typhimurium*; yeast cells; fungal cells such as *Pichia pastoris*; insect cells such as *Drosophila* and *Spodoptera* Sf9 cells; animal cells such as Chinese hamster ovary (CHO) cells, SP2/0 (mouse myeloma), human lymphoblastoid, COS, NS0 (mouse myeloma), 293T, bowes melanoma cells, HT-1080, baby hamster kidney (BHK) cells, human embryonic kidney cells (HEK), and PERC.6 (human retinal cell); or plant cells.

The composition may be used in genome editing of prokaryotic cells or eukaryotic cells. The eukaryotic organism may be one selected from eukaryotic cells (for example, fungi like yeast or cells derived from an eukaryotic animal and/or eukaryotic plant (for example, embryonic cells, stem cells, somatic cells, reproductive cells, etc.), eukaryotic animals (for example, vertebrates or invertebrates, more specifically, primates such as humans and monkeys, etc., mammals including dogs, pigs, cows, sheep, goats, mice, rats, etc.), and eukaryotic plants (for example, algae such as green algae, monocotyledon or dicotyledon plants such as coms, beans, wheat, and rice). Preferably, the composition may be used for prime editing of eukaryotic cells or eukaryotic organisms.

A cell library prepared herein refers to a cell group into which an oligonucleotide including a pegRNA-encoding sequence and a target sequence, is introduced. In this regard, an oligonucleotide having a different pegRNA-encoding sequence and/or target sequence may be introduced into each cell.

A prime editor may be introduced into the cell library to induce prime editing. The prime editor may mean a Cas9 nickase-RT fusion protein. The prime editor may be introduced into a cell by a vector or may be introduced into a cell by itself, and a method of introduction is not limited as long as the prime editor may exhibit activity in the cell. In this regard, description of the vector is as described above.

In the cell library, prime editing may occur by an introduced oligonucleotide including a pegRNA and a target sequence, and an introduced prime editor. That is, gene editing may occur for the introduced target sequence.

A method of obtaining DNA from a cell library into which the prime editor is introduced may be performed by using various DNA separation methods known in the related art.

Since gene editing is expected to have occurred at the introduced target sequence in each cell constituting the cell library, the target sequence may be sequenced to detect gene editing efficiency. The sequence analysis method is not limited to a specific method within a range that prime editing efficiency data may be obtained, but for example, deep sequencing utilizing next generation sequencing (NGS) may be used.

Another aspect provides a kit for editing the Z-type mutation of the SERPINA1 gene including the above composition.

The kit may not only include materials that allow expression of recombinant vectors to be exhibited or promoted or a composition for medium that maintains the cells, but also include a composition capable of facilitating production of recombinant vectors or introduction of recombinant vectors into a cell, and a manual for preparation of recombinant vectors or introduction of recombinant vectors into a cell. In addition, the kit may be a detection kit for detecting the Z-type mutation of the SERPINA1 gene, including the composition.

Another aspect provides a pharmaceutical composition for treatment or prevention of alpha-1 antitrypsin deficiency, including the above composition.

The alpha-1 antitrypsin deficiency is known to be generated from the liver, and is known as one of genetic disorders caused by a deficiency of a protein called alpha-1 antitrypsin (A1AT), which serves to protect the lungs and various organs from proteolytic enzymes secreted from neutrophils, a type of white blood cell, in response to infection and inflammation in the body.

The composition according to the above aspect is capable of editing a genome that induces a Z-type mutation of the SERPINA1 gene that induces alpha-1 antitrypsin deficiency, and therefore, the composition according to an aspect may be a pharmaceutical composition or a cell therapeutic agent for treating or preventing lung diseases, such as chronic obstructive pulmonary disease and emphysema, caused by a deficiency of alpha-1 antitrypsin in the blood, or liver diseases such as liver damage, cirrhosis, jaundice, hepatomegaly, and liver cancer caused by accumulation of abnormal alpha-1 antitrypsin in hepatocytes. Therefore, the alpha-1 antitrypsin deficiency may be, for example, a lung disease such as chronic obstructive pulmonary disease and/or emphysema, and a liver disease selected from liver damage, cirrhosis, jaundice, hepatomegaly, and liver cancer.

The term "prevention" refers to all actions for preventing alpha-1 antitrypsin deficiency by eliminating or early detecting a cause of the disease.

The term "treatment" refers to any action that improves or beneficially alters symptoms caused by alpha-1 antitrypsin deficiency.

The pharmaceutical composition for preventing or treating alpha-1 antitrypsin deficiency may include at least one pharmaceutically acceptable carrier such as saline, sterile water, Ringer's solution, buffered saline, cyclodextrin, a dextrose solution, a maltodextrin solution, glycerol, ethanol, liposome, and a mixture thereof, in addition to the recombinant vector, and may further include other additives in the art such as antioxidants and buffers, as needed. In addition, diluents, dispersants, surfactants, binders, and/or lubricants may be additionally added to formulate the composition into a formulation for injections, such as aqueous solutions, suspensions, emulsions, etc., or as pills, capsules, granules or tablets. Furthermore, the composition may be preferably formulated depending on each of the components by using appropriate methods in the art or methods disclosed in Remington's Pharmaceutical Science (Mack publishing company, Easton PA). The pharmaceutical composition of the present disclosure is not limited to particular formulations, but is preferably formulated into injections, eye drops or inhalants.

An administration method of the pharmaceutical composition according to an aspect is not particularly limited, but the composition may be administered orally or parenterally, via intravenous, subcutaneous, or intraperitoneal routes, or by inhalation or topical application, depending on a desired method. A dose have a wide range according to the patient's weight, age, sex, health, diet, administration time, administration manner, excretion rate, and severity of the disease. A dose means a sufficient amount of the therapeutic material according to an aspect which is administered to a subject that requires treatment to alleviate symptoms of the disease. An effective amount of the therapeutic material may vary according to the specific compound, state and severity of the disease, the subject requiring treatment, and may be determined by those skilled in the art. As a non-limiting example, a dose of the composition according to an aspect to a human subject may vary according to the patients age, body weight, sex, administration form, health, and severity of the disease. An effective amount of the therapeutic material may vary according to the specific compound, state and severity of the disease, the subject requiring treatment, and may be determined by those skilled in the art. As a non-limiting example, a dose of the composition according to an aspect to a human subject may vary according to the patients age, body weight, sex, administration form, health, and severity of the disease. The effective amount of the pharmaceutical composition may be about 0.1 μg to about 2 g, about 0.5 μg to about 1 g, about 1 μg to about 500 mg, about 10 μg to about 100 mg, or about 100 μg to about 50 mg.

A dose of the pharmaceutical composition for an adult may be, for example, about 0.001 μg/kg to about 10,000 μg/kg, about 0.01 μg/kg to about 10,000 μg/kg, about 1 μg/kg to about 100,000 μg/kg, about 1 μg/kg to about 1,000,000 μg/kg, about 10 μg/kg to about 1,000,000 μg/kg, about 0.0001 μg/kg to about 10,000 μg/kg, about 0.001 mg/kg to about 100 mg/kg, about 0.01 mg/kg to about 10 mg/kg, or about 0.1 mg/kg to about 1 mg/kg, and the dose may be administered once a day or several times a day in aliquots at a regular interval.

The term "subject" means a subject in need of treatment for a genetic disease, specifically alpha-1 antitrypsin deficiency, and more specifically, a human or a non-human primate, a mammal such as a mouse, a rat, a dog, a cat, a horse, and cattle.

The term "cell therapeutic agent" refers to a therapeutic agent using autologous, allogenic, or xenogenic cells for restoring tissue function, and to a therapeutic agent used to inhibit alpha-1 antitrypsin deficiency. When a composition including both a Cas9 nickase-RT fusion protein, which is a prime editor protein for editing a Z-type mutation of the SERPINA1 gene, and a pegRNA, is included as an active ingredient, the therapeutic agent may be used for treatment and prevention of alpha-1 antitrypsin deficiency.

The cell therapeutic agent may further include a pharmaceutically acceptable carrier. The pharmaceutically acceptable carrier may include, for example, saline, sterile water, Ringer's solution, buffered saline, cyclodextrin, a dextrose solution, a maltodextrin solution, glycerol, ethanol, human serum albumin (HSA), and a mixture thereof, and other additives in the art such as antioxidants, buffers, and bacteriostats may be further included as required.

In addition, the cell therapeutic agent, when necessary according to its formulation, may appropriately include suspending agents, solubilizing agents, stabilizers, isotonic agents, preservatives, anti-adsorption agents, surfactants, diluents, excipients, pH adjusters, analgesic agents, buffers, sulfur-containing reducing agents, antioxidants, and the like. Examples of the suspending agents include methyl cellulose, polysorbate 80, hydroxyethyl cellulose, gum Arabic, tragacanth, carboxymethyl cellulose sodium, and polyoxyethylene sorbitan monolaurate.

Examples of the solubilizing agents include polyoxyethylene hydrogenated castor oil, polysorbate 80, nicotinic acid amide, polyoxyethylene sorbitan monolaurate, macrogol, and castor oil fatty acid ethyl ester. The stabilizers may include dextran 40, methylcellulose, gelatin, sodium sulfite, sodium metasulfate.

Examples of the isotonic agents include D-mannitol and sorbitol.

The preservatives may include, for example, methyl paraoxybenzoate, ethyl paraoxybenzoate, sorbic acid, phenol, cresol, chlorocresol, and the like.

The anti-adsorption agents may include human serum albumin, lecithin, dextran, ethylene oxide propylene oxide copolymer, hydroxypropyl cellulose, methyl cellulose, polyoxyethylene hydrogenated castor oil, polyethylene glycol, and the like.

Examples of the sulfur-containing reducing agents include, for example, those having a sulfhydryl group such as N-acetylcysteine, N-acetylhomocysteine, thioctoic acid, thiodiglycol, thioethanolamine, thioglycerol, thiosorbitol, thioglycolic acid and salts thereof, sodium thiosulfate, glutathione, and thioalkanoic acids having 1 to 7 carbon atoms.

Antioxidants may include, for example, chelating agents such as erythorbic acid, dibutylhydroxytoluene, butylhydroxyanisole, α-tocopherol, tocopherol acetate, L-ascorbic acid and its salts, L-ascorbic acid palmitate, L-ascorbic acid stearate, sodium hydrogensulfite, sodium bisulfite, sodium sulfite, triamyl gallic acid, propyl gallic acid, sodium ethylenediaminetetraacetate (EDTA), sodium pyrophosphate, sodium metaphosphate, and the like.

In addition, the cell therapeutic agent may be administered once a day or several times a day in aliquots at a regular interval, or several times at a regular interval, in an amount of, for example, about 1,000 cells/time to about 10,000 cells/time, about 1,000 cells/time to about 100,000 cells/time, about 1,000 cells/time to about 1,000,000 cells/time, about 1,000 cells/time to about 1000 cells/time 10,000,000, about 1,000 cells/time to about 100,000,000 cells/time, about 1,000 cells/time to about 1,000,000,000 cells/time, about 1,000 cells/time to about 10,000,000,000 cells/time, based on an adult patient with a body weight of 70 kg.

An injection product according to the present disclosure may be prepared in a form of a pre-filled syringe by taking an amount commonly known in the art, according to patient's constitution and a type of disorder.

Still another aspect provides a method of editing the Z-type mutation of the SERPINA1 gene, the method including introducing respective recombinant vectors into isolated eukaryotic cells or eukaryotic organisms except for human, wherein the recombinant vectors include: a recombinant vector expressing a prime editor protein or a variant of the prime editor protein, the prime editor protein including a nucleic acid sequence encoding a Cas9 nickase-reverse transcriptase; and a recombinant vector including a prime editing guide RNA (pegRNA) sequence.

The introduction of the recombinant vector may be carried out by one method selected from the group consisting of local injection, microinjection, electroporation, and lipofection.

The composition may be used in genome editing of prokaryotic cells or eukaryotic cells. The eukaryotic organism may be one selected from eukaryotic cells (for example, fungi like yeast or cells derived from an eukaryotic animal and/or eukaryotic plant (e.g., embryonic cells, stem cells, somatic cells, reproductive cells, etc.)), eukaryotic animals (for example, vertebrates or invertebrates, more specifically, primates such as humans and monkeys, etc., mammals including dogs, pigs, cows, sheep, goats, mice, rats, etc.), and eukaryotic plants (for example, algae such as green algae, monocotyledon or dicotyledon plants such as corns, beans, wheat, and rice).

All processes performed in the method of genome editing may be carried out in the cells or outside the cells, or in vivo, or ex vivo.

The method of genome editing may be performed by prime editing.

The same terms and elements mentioned in the description of the method of genome editing to those beforehand mentioned are as described above.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Example 1. Preparation of Lentiviral Vector from Oligonucleotide Library 1.1 Construction of Plasmid Vector Expressing Prime Editor In order to prepare a plasmid expressing a prime editor, a plasmid vector expressing an NGG-PAM prime editor was constructed by using prime editor 2 (PE2) (Addgene No. 132775) having a lentiviral promoter. In addition, a plasmid vector expressing an NG-PAM prime editor was constructed. In addition, the plasmid vector expressing the prime editor was constructed to express a gene resistant to an antibiotic Blasticidin.

The plasmid vector expressing lentiviral NGG-PAM prime editor was prepared by the following method. First, LentiCas9-Blast plasmids (Addgene No. 52962) were digested with restriction enzymes, Age1 and BamH1, (by NEB Company) at 37° C. for 4 hours or more. In order to prevent cleavage sites of the digested product from being ligated again, 1 μl of NEB's Quick-CIP was added, followed by incubation at 37° C. for additional 10 minutes. Next, the linearized plasmids were identified on agarose gel and then purified by using a MEGAquick-spin Total Fragment DNA Purification kit (by iNtRON biotechnology). A product in which pCMV-PE2 (Addgene No. 132775) was amplified for 30 cycles by using NEB Phusion polymerases (Catalog No.: M0530L) was Gibson ligated with the linearized LentiCas9-Blast plasmid (using the NEB's 2×HIFI DNA assembly master mix), and finally, a plasmid vector expressing lentiviral NGG-PAM prime editor (NGG-PAM-Cas9 nickase H840A, SEQ ID NO: 5) was constructed.

The plasmid vector expressing an NG-PAM prime editor was prepared by the following method. Lenti_Split-BE4-N-Blast plasmids were prepared as follows. BE4 plasmids (Addgene No. 100802) and intein-mediated split cas9 plasmids (see Truong, D. J. et al. Development of an intein-mediated split-Cas9 system for gene therapy. Nucleic Acids Res. 43, 6450-6458 (2015)) were amplified for 30 cycles by using NEB phusion polymerases (Catalog No.: M0530L), and then inserted together to lenticas9-blast (Addgene no. 52962) by Gibson assembly (using the NEB's 2×HIFI DNA assembly master mix), to prepare a final product of Lenti_split-BE4-N-Blast. The Lenti_Split-BE4-N-Blast plasmids were digested with restriction enzymes, Age1, and BamH1, (by NEB). Then, the linearized plasmids were identified on agarose gel and then purified by using a MEGAquick-spin Total Fragment DNA Purification kit (iNtRON biotechnology). pCMV-PE2 (Addgene No. 132775) and NG-ABEmax plasmids (124163) were amplified for 30 cycles by using NEB phusion polymerases (Catalog No.: M0530L), and then Gibson ligated (NEB's 2×HIFI DNA assembly master mix) with the linearized Lenti_Split-BE4-N-Blast plasmids, to finally prepare plasmid vectors expressing an NG-PAM prime editor (NG-PAM-Cas9 nickase H840A, SEQ ID NO: 6).

1.2 Production of Oligonucleotide Library

An oligonucleotide library (twist bioscience) including a pegRNA for correction of a Z-type mutation of alpha-1 antitrypsin deficiency was used. Each of the prepared oligonucleotides included in the library consisted of a pegRNA sequence for correction of the mutation, a mutation sequence, and a pair of barcode sequences unique to the oligonucleotide, and a library including a total of 237 different pegRNAs was constructed. The barcode sequence is a random sequence arbitrarily inserted into an oligonucleotide and has a length of 10 to 20 base pairs, and each prepared oligonucleotide has a unique barcode sequence, and it is known that barcode sequences allow finding information of the oligonucleotide in NGS results with easiness, or distinguishing between duplicates. In addition, the pegRNA was prepared to additionally include spacers, reverse transcriptase (RT) templates, and primer binding sites (PBSs) of different sequences.

1.3 Plasmid Library Construction

PCR amplification was performed on individual sequences of the oligonucleotide library prepared in the above example by using the NEB Phusion polymerases (catalog number: M0530L).

Figure 1:
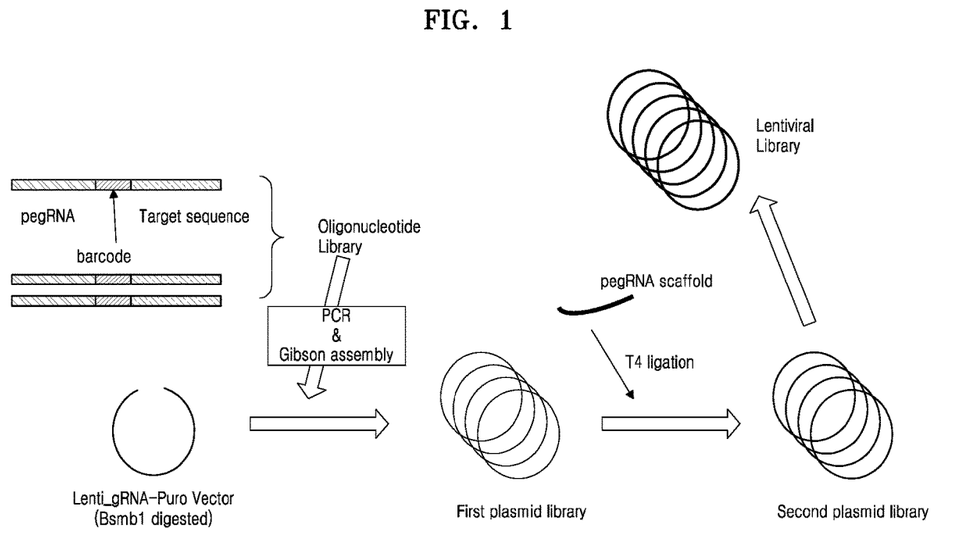
FIG. 1 is a diagram schematically illustrating a method of obtaining a lentiviral library from an oligonucleotide library including a pegRNA for correction of a Z-type mutation of alpha-1 antitrypsin deficiency.
Figure 2:
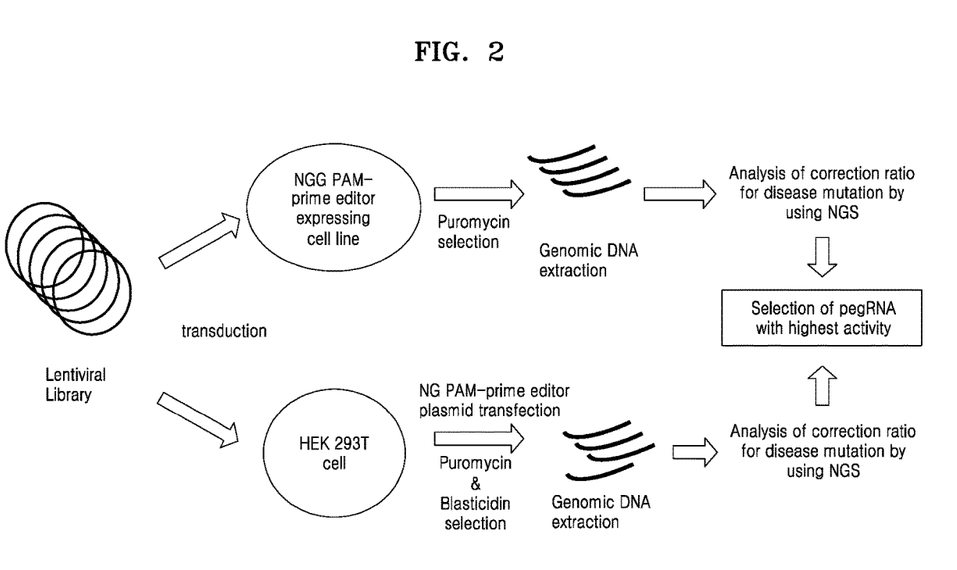
FIG. 2 is a diagram schematically illustrating a method of identifying an optimized pegRNA having the highest correction efficiency through cell experiments and next generation sequencing (NGS) analysis using the lentivirus library.

Lenti_gRNA-Puro vectors (Addgene no. 84752) were digested with BsmB1 enzymes at 55° C. for 6 hours. Thereafter, the product was loaded on agarose gel and electrophoresed to separate vector backbones of an appropriate size (by using an Intron biotechnology fragment DNA purification kit). Oligonucleotides ordered from Twist bioscience were amplified for 14 cycles using the NEB Phusion polymerases. Then, as in the above process, after loading on agarose gel, electrophoresis was performed to separate inserts of an appropriate size. Gibson assembly was performed on the inserts separated from the vector backbones (using NEB's 2×HIFI DNA assembly master mix). Endura electrocompetent cells (Lucigen) were transformed with the finally selected first plasmid library by electroporation. Thereafter, the transformed bacteria were cultured overnight in LB medium including carbenicillin. After harvesting the bacteria from the medium, a first library of 576 plasmids was harvested by using Qiagen's midi-prep kit. The harvested first plasmid library was enzyme-digested for 6 hours by using bsmb1. The product of the cleavage was loaded on agarose gel and separated by electrophoresis. The separated product was cloned with pegRNA scaffold oligonucleotides at 16° C. for 6 hours by using T4 ligation to select a second plasmid library, and as with the first plasmid library, endura electrocompetent cells (lucigen) were transformed with the second plasmid library, and the transformed bacteria were cultured overnight in LB medium including carbenicillin. After harvesting the bacteria from the medium, a second library of 576 plasmids was harvested by using Qiagen's midi-prep kit. A method of producing a specific plasmid library is shown in a schematic diagram of FIG. 1.

Example 2. Confirmation of Optimal pegRNA Sequence by Using the Prepared Lentiviral Library 2.1 Confirmation of Optimal pegRNA for Correcting Alpha-1 Antitrypsin Deficiency Z Mutant Gene A lentiviral library was prepared by transfecting HEK293T cells with the second library of 576 plasmids prepared in Example 1.3 together with psPAX2 (Addgene no. 12260) and pMD2.G (Addgene No. 12259). Then, the lentiviral library was transfected into HEK293T cells expressing NGG-PAM prime editors, or normal HEK293T cells.

The HEK293T cells expressing NGG-PAM prime editors were constructed by using the plasmid vectors expressing NGG-PAM prime editors having the lentiviral promoter of Example 1.1.

Genomic DNA of the lentiviral library group transfected into HEK293T cells expressing NGG-PAM prime editors was obtained after culturing the cells in a medium containing puromycin for about 7 days.

The lentiviral library group transfected into normal HEK293T cells were cultured in a medium containing puromycin for about 7 days, then the plasmid vectors expressing NG-PAM prime editors of Example 1.1 were transfected, the cells were cultured in a medium containing blasticidin for about 5 days, and then genomic DNA was obtained.

Figure 3:
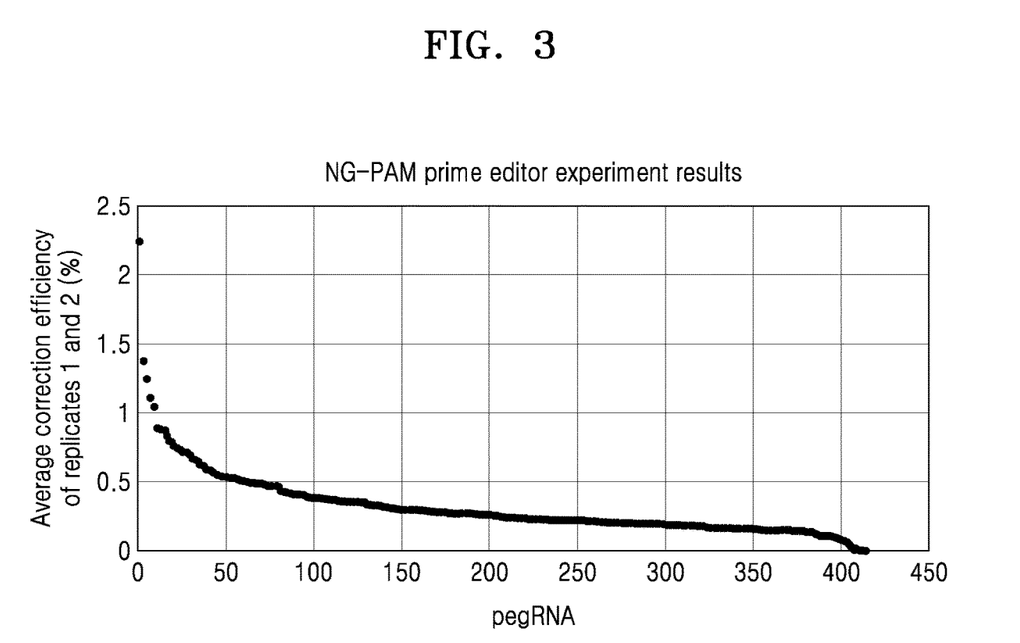
FIG. 3 is a diagram confirming correction efficiencies for the Z-type mutation of alpha-1 antitrypsin deficiency in Replicate Experiments 1 and 2 by using NGG-PAM prime editor 2 in a pegRNA library.
Figure 4:
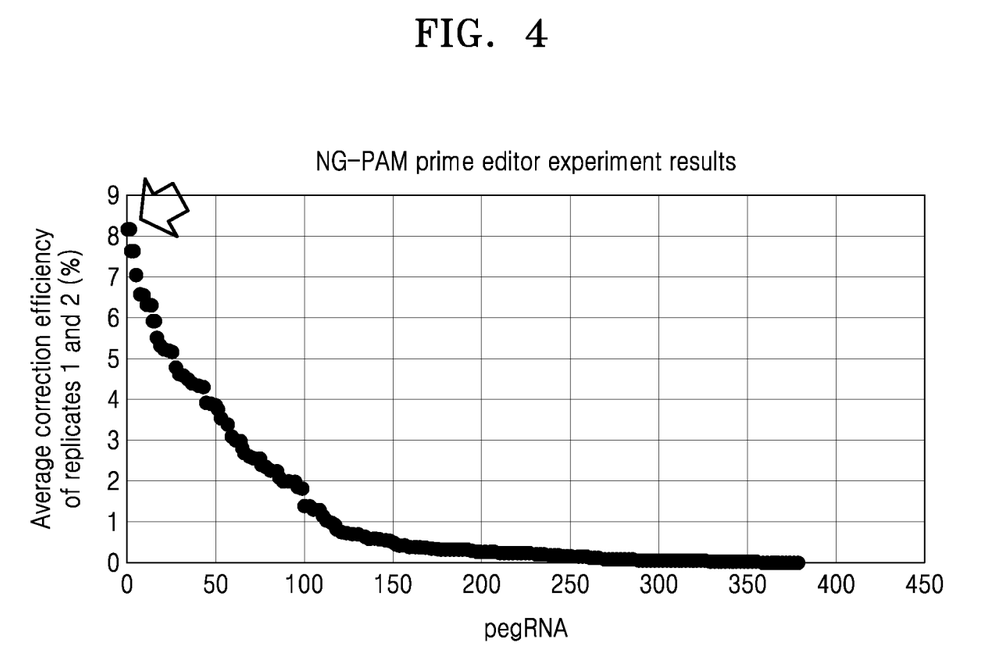
FIG. 4 is a diagram confirming correction efficiencies for the Z-type mutation of alpha-1 antitrypsin deficiency in Replicate Experiments 1 and 2 by using NG-PAM prime editor 2 for a pegRNA library.

The genomic DNA obtained from the cell pool in which gene correction occurred was analyzed by using next generation sequencing (NGS), and the mutation correction efficiency of each pegRNA was verified. In such correction efficiency verification, a target sequence portion is amplified by PCR and analyzed by using NGS, and as a result of this analysis, a FASTQ file in which a 'barcode-unedited target sequence' and a 'barcode-edited target sequence' were mixed was obtained. Then, in order to confirm gene editing efficiency of a specific pegRNA, first, all reads having a barcode corresponding to the pegRNA and the "edited" target sequence were counted. Next, gene editing efficiency of the specific pegRNA was calculated by dividing the read count by a number of all (unedited+edited) reads having the corresponding barcode. Through this process, results of confirming a mutation correction efficiency of a pegRNA with an NGG-PAM prime editor are shown in FIG. 3, and results of confirming a mutation correction efficiency of a pegRNA with an NG-PAM prime editor is shown in FIG. 4. In these results, results with reads less than 200 were excluded from the analysis.

As confirmed in FIG. 3, as a result of confirming the mutation correction efficiency confirmed through NGG-PAM PE2 with an average correction efficiency of Replicate Experiment 1 and Replicate Experiment 2, it was confirmed that there was no pegRNA having gene editing ability high enough to correct an alpha-1 antitrypsin deficiency Z mutant gene to a significant degree.

As confirmed in FIG. 4, the mutation correction efficiency confirmed through NG-PAM PE2 was confirmed with an average correction efficiency of Replicate Experiment 1 and Replicate Experiment 2, and a pegRNA showing a relatively high degree of editing efficiency was confirmed, and is indicated by an arrow. The average correction efficiency of the pegRNA confirmed by using NG-PAM PE2 was 8.155% as an average of Replicate Experiments 1 and 2, and it was specifically confirmed that the alpha-1 antitrypsin deficiency Z mutant gene may be effectively corrected.

2.2 Confirmation of Optimal pegRNA Sequence

The optimal pegRNA for correcting the Z-type mutation of alpha-1 antitrypsin deficiency was confirmed by using a prime editor confirmed in Example 2.1, and a sequence of the optimal pegRNA is shown in Table 1 above.

Through the above results, it was confirmed that delivery of a gene editing body of a lentiviral vector-mediated NG-PAM PE2 with the optimal pegRNA may induce exquisite genome editing in an organism or a cell with an alpha-1 antitrypsin deficiency Z-type mutation. The above results show that the composition according to an aspect may effectively edit a genome of an organism having the alpha-1 antitrypsin deficiency Z-type mutation, and may be useful for treating alpha-1 antitrypsin deficiency, a genetic disease caused by mutations in a SERPINA1 gene. Therefore, the composition according to an aspect acts specifically on a target sequence of the SERPINA1 gene and enables genome editing with high accuracy, and therefore, is expected to be useful as a SERPINA1 gene editing platform.

The composition according to an aspect includes both a pegRNA sequence capable of effectively editing the SERPINA1 gene and PE 2, and thus, may effectively deliver the prime editor to a cell, and act specifically for a target sequence of the SERPINA1 gene, enabling genome editing with high accuracy, and therefore, may be usefully used as a SERPINA1 gene editing platform. In addition, the composition is capable of correcting a Z-type mutation of the SERPINA1 gene, and may be used for treatment or prevention of alpha-1 antitrypsin deficiency.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A composition for editing a Z mutation of an SERPINA1 gene, comprising: a recombinant vector expressing a prime editor protein, the prime editor protein comprising a nucleic acid sequence encoding a Cas9 nickase-reverse transcriptase; and a recombinant vector comprising a prime editing guide RNA (pegRNA) sequence, wherein each respective recombinant vector is selected from the group consisting of a lentiviral vector, a retroviral vector, an adenoviral vector, and a herpes simplex viral vector, wherein the nucleic acid sequence encoding the Cas9 nickase-reverse transcriptase consists of the nucleotide sequence of SEQ ID NO: 6, and wherein the pegRNA sequence consists of the nucleotide sequence of SEQ ID NO: 1.

2. A kit for editing a Z mutation of an SERPINA1 gene comprising the composition of claim 1.

3. A pharmaceutical composition for treatment or prevention of alpha-1 antitrypsin deficiency, comprising the composition of claim 1.

4. A method of editing a Z mutation of an SERPINA1 gene, the method comprising: introducing respective recombinant vectors into isolated eukaryotic cells; or eukaryotic organisms except for human, wherein the recombinant vectors comprise: a recombinant vector expressing a prime editor protein, the prime editor protein comprising a nucleic acid sequence encoding a Cas9 nickase-reverse transcriptase; and a recombinant vector comprising a prime editing guide RNA (pegRNA) sequence, wherein each respective recombinant vector is selected from the group consisting of a lentiviral vector, a retroviral vector, an adenoviral vector, and a herpes simplex viral vector, wherein the nucleic acid sequence encoding the Cas9 nickase-reverse transcriptase consists of the nucleotide sequence of SEQ ID NO: 6, and wherein the pegRNA sequence consists of the nucleotide sequence of SEQ ID NO: 1.

5. The method of claim 4, wherein, the introduction of the respective recombinant vectors is carried out by a method selected from the group consisting of microinjection, electroporation, and lipofection.

* * * * *